US005748598A

United States Patent [19]
Swanson et al.

[11] Patent Number: 5,748,598
[45] Date of Patent: May 5, 1998

[54] APPARATUS AND METHODS FOR READING MULTILAYER STORAGE MEDIA USING SHORT COHERENCE LENGTH SOURCES

[75] Inventors: Eric A. Swanson, Acton; Stephen R. Chinn, Westford, both of Mass.

[73] Assignee: Massachusetts Institute of Technology, Cambridge, Mass.

[21] Appl. No.: 577,366

[22] Filed: Dec. 22, 1995

[51] Int. Cl.⁶ .................................................. G11B 3/74
[52] U.S. Cl. .............................................. 369/94; 369/100
[58] Field of Search ................................ 369/94, 112, 109, 369/93, 99, 100, 116, 120, 121

[56] References Cited

U.S. PATENT DOCUMENTS

| | | | |
|---|---|---|---|
| 3,905,703 | 9/1975 | Matsumoto | 356/106 R |
| 3,912,391 | 10/1975 | Fleisher et al. | 355/54 |
| 4,160,269 | 7/1979 | Kramer et al. | 365/124 |
| 4,161,752 | 7/1979 | Basilico | 358/128 |
| 4,253,019 | 2/1981 | Opheij et al. | 369/44.11 |
| 4,253,723 | 3/1981 | Kojima et al. | 350/3.72 |

(List continued on next page.)

FOREIGN PATENT DOCUMENTS

| | | | |
|---|---|---|---|
| 0446063 A1 | 9/1991 | European Pat. Off. | G11B 7/24 |
| 0511023 A1 | 10/1992 | European Pat. Off. | G11B 7/00 |
| 0 605 924 A2 | 7/1994 | European Pat. Off. | G11B 7/24 |
| 61-227237 | 10/1986 | Japan | G11B 7/135 |
| 61-240447 | 10/1986 | Japan | G11B 7/135 |
| 7049306 | 2/1995 | Japan | G01N 21/45 |

OTHER PUBLICATIONS

S.R. Chinn et al., "Multi-Layer Optical Readout Using Direct or Interferometic Detection and Broad-Bandwidth Light Sources" *Optical Memory and Neural Networks* 5(3):197–217 (1996).

International Search Report dated May 16, 1997 in corresponding PCT application serial number PCT/US96/19950.
K. Baba et al., "Three–Dimensional Optical Disks Using Metallic Island Films: A Proposal", *Electronic Letters* 28(7) (1992).
I.B. Rudakov et al., "Multilayer Optical Information Recording", *Optoelectronics, Instrumentation and Data Processing*, No. 3 (1991).
P.J. Brock et al., "Fabrication of Grooved Glass Substrates by Phase Mask Lithography", *J. Vac. Sci. Tech.* B9(6) (1991).
Yamada et al., "Pit Shape at Overwriting of Thermal Magneto–Optical Recording", *SPIE Optical Storage Tech. & Applns.* 899 (1988).
Zhov et al., "Optimization of Information Pit Shape and Read–Out System in Read–Only and Write–Once Optical Storage Systems" *Applied Optics* 27(4) (1988).
D.S. Marx et al., "Pit Depth Encoded Memories", *Optical Data Storage* 2338 (1994).
M. Itonaga et al., "Master Recording Using Kr Ion Laser", *Jap. J. of Applied Physics* 31(1, No. 2B) (1992).

*Primary Examiner*—Paul W. Huber
*Attorney, Agent, or Firm*—Testa, Hurwitz & Thibeault, LLP

[57] ABSTRACT

Apparatus and methods for reading multilayer optical data storage media are described. The apparatus includes a short coherence length light source and an optical system. The optical system focuses the light from the source onto the layers of the storage media. The coherence length of the source is less than 100 microns or less than the spacing between the layers. The Rayleigh range within the storage media may also be less than the spacing between the layers. The apparatus may include a detector for measuring alterations in light reflected from each layer of the storage media caused by data. The source may be any short coherence length source including superluminescent diodes, mode locked lasers, multi-longitudinal mode laser diode, or rare earth doped amplified spontaneous emission sources.

26 Claims, 3 Drawing Sheets

U.S. PATENT DOCUMENTS

| | | | |
|---|---|---|---|
| 4,360,908 | 11/1982 | Howe et al. | 369/109 |
| 4,458,345 | 7/1984 | Bjorklund et al. | 369/103 |
| 4,684,206 | 8/1987 | Bednorz et al. | 350/96.12 |
| 4,857,719 | 8/1989 | Ando | 250/201 |
| 4,870,635 | 9/1989 | Rocheter et al. | 369/215 |
| 4,900,691 | 2/1990 | Jun | 437/52 |
| 5,068,846 | 11/1991 | Kramer | 369/275.1 |
| 5,121,376 | 6/1992 | Kuder et al. | 369/100 |
| 5,126,996 | 6/1992 | Iida et al. | 369/283 |
| 5,134,604 | 7/1992 | Nagashima et al. | 369/94 |
| 5,144,603 | 9/1992 | Mozume et al. | 369/44.14 |
| 5,144,617 | 9/1992 | Gotoh et al. | 369/244 |
| 5,251,198 | 10/1993 | Strickler | 369/110 |
| 5,258,969 | 11/1993 | Refregier et al. | 369/100 |
| 5,289,454 | 2/1994 | Mohapatra et al. | 369/112 |
| 5,303,225 | 4/1994 | Satoh et al. | 369/275.3 |
| 5,327,415 | 7/1994 | Vettiger et al. | 369/121 |
| 5,373,499 | 12/1994 | Imaino et al. | 369/275.4 |
| 5,381,401 | 1/1995 | Best et al. | 369/275.1 |
| 5,428,597 | 6/1995 | Satoh et al. | 369/275.1 |
| 5,453,969 | 9/1995 | Psaltis et al. | 369/275.1 |
| 5,463,609 | 10/1995 | Inagaki et al. | 369/112 |
| 5,471,455 | 11/1995 | Jabr | 369/109 X |
| 5,477,527 | 12/1995 | Tsuchiya et al. | 369/275.4 |

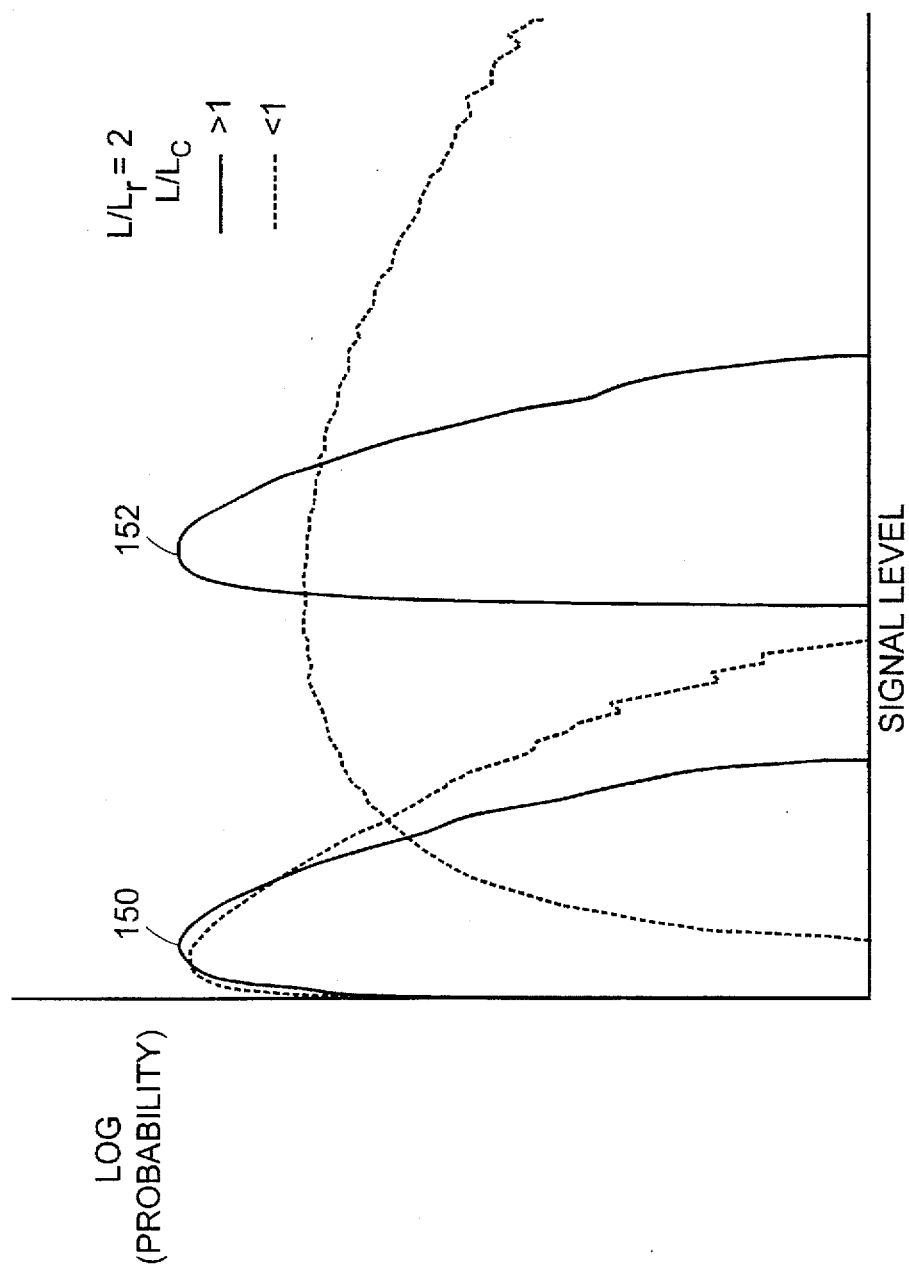

APPARATUS AND METHODS FOR READING MULTILAYER STORAGE MEDIA USING SHORT COHERENCE LENGTH SOURCES

GOVERNMENT SUPPORT

This invention was made with government support under Contract Number F19628-95-C-0002 awarded by the Air Force. The government has certain rights in the invention.

FIELD OF THE INVENTION

The invention relates generally to the field of optical data storage media and systems. In particular, the invention relates to apparatus and methods for reading optical storage media with multiple data storage layers.

BACKGROUND OF THE INVENTION

Optical data storage systems provide a means for storing large quantities of data onto relatively small and lightweight storage media. Optical storage systems have numerous advantages over competing technologies such as relatively high density and inexpensive duplication. In addition, since the read head of optical storage systems does not contact the storage media, optical storage media has long term stability.

Optical storage media can take a variety of forms including optical tape, compact disc read-only memory (CD-ROM), write-once read-many times memory (WORM), and rewritable memory. The optical tape or compact disk memory may have multiple data storage layers. For example, CD-ROM optical storage medium typically comprises a polycarbonate substrate having at least one data storage layer. Each data storage layer is coated with a reflective or partially reflective layer.

Data on a storage layer can be represented in many ways. For example, data can be represented by a series of pits, in an otherwise planar region, which are varied in length in order to code the data. When light from a read head is focused onto a data storage layer, the planar regions of the layer reflect high level optical signals and the pits reflect low level optical signals. A photosensitive detector in the read head converts the high and low level optical signals to high and low level electrical signals which represent digital data.

To increase optical storage capacity, storage media with multiple data storage layers and systems for reading such media have been proposed. The density of storage media having multiple data storage layers is, however, limited by cross-talk. Cross-talk occurs because optical signals reflected from the media contain both desirable reflections from the layer of interest and undesirable reflections from the adjacent layers. These undesirable reflections produce cross-talk which degrades performance and ultimately limits the density of stored data.

The amount of cross-talk is dependent on the coherence length of the source, the layer spacing of the storage medium, and the physical optics which define the Rayleigh range within the storage media and the imaging optics. Coherence length is a measure of the distance over which light from the source remains coherent and thus is inversely proportional to the bandwidth of a spectral emission line of the source. As the coherence length increases, the effects of cross-talk generally increase. Light emitted from a CW semiconductor laser diode is highly coherent and thus the coherence length of such sources is relatively long. Therefore, optical storage systems utilizing CW semiconductor laser diodes generally have poor volume density.

The Rayleigh range is a measure of the depth of focus of a collimated beam or equivalently, the distance that a collimated beam travels before the beam begins to diverge significantly due to diffraction spreading. The Rayleigh range is the approximate distance where the Gaussian beam diameter expands by a factor of the square root of two from the waist or narrowest point. In general, if the data storage layers are separated by many Rayleigh ranges, cross-talk will be low and the stored data may be reliably detected. As the spacing between data layers approaches a Rayleigh range, however, cross-talk increases significantly.

Techniques have been proposed to reduce cross-talk when accessing data from storage media having multiple data storage layers. For example, techniques have been proposed that utilize low coherence length sources and interferometric techniques to discriminate signals from the various layers. These techniques are relatively complex and require significant modifications to existing technology and, thus are expensive to implement. The invention described herein provides an apparatus for increasing the density of data while avoiding the problems of the prior art.

SUMMARY OF THE INVENTION

The invention relates to an apparatus for reading high density optical storage media with multiple data storage layers. By utilizing a source of light with a short coherence length and including variable focusing optics to select particular layers, an optical storage system may be constructed to read high density optical media with multiple data storage layers. This invention allows manufacturers to replace existing low-power CW laser diodes with relatively inexpensive short coherence length optical sources such as superluminescent diodes.

Accordingly, the present invention features an apparatus for reading data on an optical storage media containing at least two data storage layers in which each layer is separated by a spacing L. A data storage layer is a location at which data is stored. Typically data storage layers are planar locations. The apparatus includes a source of light having a coherence length $L_c$ that is substantially less than 100 microns. The apparatus also includes an optical system for selectively focusing the light from the source onto particular layers of the media. The apparatus also includes imaging optics and a detector for measuring alterations in the light reflected from each layer which are caused by the data.

The source may be any short coherence length source of light such as a superluminescent diode, a mode locked laser, multi-longitudinal mode laser diode, or a rare earth doped amplified spontaneous emission source. The coherence length $L_c$, may also be substantially less than 50 microns or substantially less than the layer spacing L. The layer spacing L of the optical storage media may be chosen to be greater than the Rayleigh range $L_r$, but less than one hundred times the Rayleigh range $L_r$ within the optical storage medium.

In another embodiment, the present invention features an optical storage media having at least two layers where each layer has a layer spacing L and an apparatus for reading data on the optical storage media. The apparatus includes a source of light having a coherence length $L_c$ that is substantially less than 100 microns. In addition, the apparatus includes an optical system for selectively focusing the light from the source onto particular layers of the media. The apparatus may also include a detector for measuring alterations in the light reflected from each layer which are caused by the data.

The source may be any short coherence length source of light such as a superluminescent diode, a mode locked laser, multi-longitudinal mode laser diode, or a rare earth doped amplified spontaneous emission source. The coherence length $L_c$ may also be substantially less than 50 microns or substantially less than the layer spacing L. The layer spacing L of the optical storage media may be chosen to be greater than the Rayleigh range $L_r$ within the optical storage medium, but less than one hundred times or ten times the Rayleigh range $L_r$.

In another embodiment, the present invention features a method of reading data.

The method includes providing a source of light having a coherence length $L_c$. In addition, the method includes focusing the light from the source onto a layer of an optical storage media. The optical storage media has at least two layers separated by a layer spacing L. The coherence length $L_c$ is substantially less than 100 microns. The coherence length $L_c$, may also be substantially less than 50 microns or substantially less than the layer spacing L. The method may include the step of detecting alterations in the light reflected from each layer which are caused by the data.

In another embodiment, the present invention features a method of providing and reading data from a high density optical storage media. The method includes providing an optical storage media comprising at least two layers. Each layer of the optical storage media contains data and is separated by a layer spacing L. The method also includes providing a source of light having a coherence length $L_c$, which is substantially less than 100 microns. The coherence length $L_c$ of the light source provided may also be substantially less than 50 microns or substantially less than the layer spacing L. In addition, the method includes focusing the light from the source of light onto a layer of the optical media. The method may include the step of detecting alterations in the light reflected from each layer caused by the data.

BRIEF DESCRIPTION OF THE DRAWINGS

The foregoing and other objects, features and advantages of the invention will become apparent from the following more particular description of preferred embodiments of the invention, as illustrated in the accompanying drawings.

FIG. 3 illustrates results of theoretical calculations of approximate normalized signal probabilities density function for an optical storage system having cross-talk from two adjacent layers on either side of the desired data storage layer.

DETAILED DESCRIPTION

Figure 1:
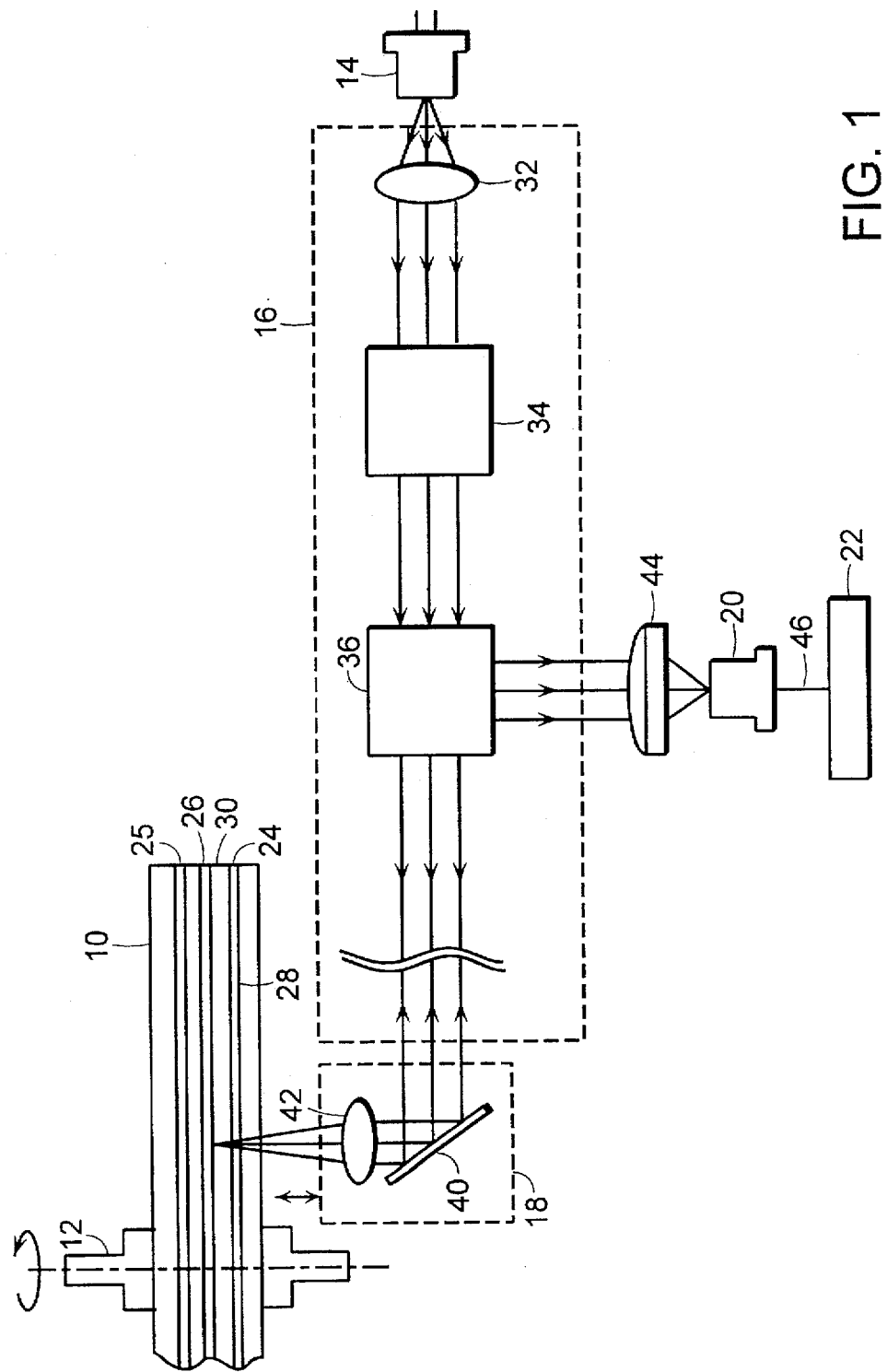
FIG. 1 is a schematic diagram of an embodiment of an optical storage apparatus for reading information stored on multiple data storage layers of an optical storage medium.

FIG. 1 is a schematic diagram of an embodiment of an optical storage apparatus for reading information stored on multiple data storage layers of an optical storage medium. Generally, the optical storage apparatus includes a multilayered optical storage medium 10, a media drive system 12, a light source 14, an optical system 16, a variable focus optical read head 18, a detector 20 and a computer interface 22.

In this embodiment, the multilayered optical storage medium 10 is a disk with at least two data storage layer 24–26 wherein each layer comprises a series of data pixels (not shown) on an otherwise partially reflective surface 28. In other embodiments, the optical storage medium 10 may be a multilayer optical tape. The data pixels may represent information, images, or audio. Each data pixel may have more than two possible values of reflectivities and thus, may contain multiple bits per pixel which is herein defined as M-ary storage. For example, in one embodiment, the data pixels may be pits with multiple values of reflectivities caused by varying pit depths. In other embodiments, the data pixels may be sites of media phase changes or magnetooptic effects.

The data storage layers 24–26 may be any generally planar location where data is stored. The data storage layers have a layer spacing 30. In one embodiment, the layer spacing L of the optical storage medium 10 is chosen to be greater than the Rayleigh range within the optical storage medium 10. In another embodiment, the layer spacing is chosen to be greater than the Rayleigh range within the optical storage medium 10 and less than one hundred times the Rayleigh range $L_r$. The drive system 12 rotates the medium 10 at a predetermined speed.

The light source 14 has a coherence length $L_c$ that is substantially less than 100 microns. The coherence length $L_c$, of the light source 14 may also be substantially less than 50 microns or substantially less than the layer spacing 30. The light source 14 may be any relatively short coherence length source such as a superluminescent diode, a mode locked laser, multi-longitudinal mode laser diode, or a rare earth doped amplified spontaneous emission source.

The optical system 16 and the variable focus optical read head 18 focuses light from the light source 14 onto the medium 10. Collimating optics 32 are used to collimate the diverging light beam emitted from the light source 14. Circularizing optics 34 may be utilized to generate a circular profile for the collimated light beam. In this embodiment, a polarization beamsplitting cube 36 distinguishes the light beam incident from the light source 14 from the light beam reflected from the optical storage medium 10 which contains the data. Other techniques for distinguishing these light beams, such as the use of a quarter-wave plate, are well known in the art.

The variable focus optical read head 18 includes a steering mirror 40 and at least one objective lens 42. The read head 18 selectively focuses the light beam from the source 14 onto a series of pits (not shown) which represent the desired data on the particular layer of the medium 10. Focusing is accomplished by adjusting the location of the objective lens 42 so that the focal point is on the desired data storage layer 26. The location of the objective lens may be adjusted by a lens positioning system (not shown) and a tracking and control circuit (not shown). Astigmatic lenses with quad cells may be used for maintaining tracking and focus as is well known in the art. The steering mirror 40 directs the focused light beam to the desired data on the desired data storage layer 26.

The planar portions of the layer (not shown) partially reflect the light beam back to the objective lens 42 with low loss. The pits (not shown) partially reflect the light beam out of phase with respect to light reflected from planar regions of the data storage layer. The steering mirror 40 directs the partially reflected light beam from the objective lens 42 back to the polarization beamsplitting cube 36.

The polarizing beamsplitter 36 reflects the rotated light beam to a lens 44 which focuses the light beam to the detector 20. In another embodiment, a near-diffraction limited receiver (not shown) is utilized to detect the reflected light beam which contains the data. Such a receiver will allow only a substantially single spatial mode to be detected. This minimizes the sensitivity to out-of-focus or stray light and thus further reduces cross talk. Such receivers are well known in the art, and for example, may comprise a single mode optical fiber. In such a receiver, it is the mode overlap of the desired data layer and the interfering data layer, both spectrally and spatially, that determines overall system performance.

The detector 20 converts the light reflected from the storage medium 10 to an electronic signal. An output 46 of the detector 20 is electrically coupled to the computer interface 22 which converts the electronic signal to the desired digital data. The output 46 of the detector 20 is a photocurrent which is proportional to an optical intensity (not shown) focused on the detector 20. The optical intensity can be described by the magnitude squared of a complex field amplitude. The complex field is the sum of a desired field from the particular storage layer 24 and cross-talk fields reflected from all of the other data storage layers 24-26. Cross-talk fields received by the detector 20 from layers other than the particular storage layer 24 are reduced by a geometric defocusing factor and by reflective modulation from the undesired data pattern. The total received field is a complex (phasor) sum of the desired field plus all reduced cross-talk fields.

If the light source 14 is coherent, the desired field and cross-talk fields add in a complex vector manner, with interference-like behavior to form the total received field. The total received field intensity can have large fluctuations as the phases in the cross-talk fields vary. As the source becomes incoherent, however, interference effects disappear and the total received field intensity becomes the sum of desired field intensity plus individual cross-talk intensities. The addition of individual intensities, rather than the square of the sum of complex phase-fluctuating amplitudes, significantly reduces the cross-talk fluctuations from the coherent case. This reduction in cross-talk fluctuations allows data layers to be spaced more closely together and thus improves optical storage density.

The amount of cross-talk is dependent on the coherence length of the source, the layer spacing 30, and the Rayleigh range within the storage medium 10 and the imaging optics. Coherence length is a measure of the distance over which light from the source 14 remains coherent and thus is inversely proportional to the bandwidth of a spectral emission line of the source 14. For a spectrum with a Gaussian intensity distribution, the coherence length can be defined in terms of a resulting Gaussian autocorrelation (fringe visibility) function $$R(\Delta x) = \exp[-(\Delta x/L_c)^2].$$

If the light from the source 14 is monochromatic and thus highly coherent, the coherence length is relatively long. If the light from the source 14 has a broad incoherent spectrum, however, the coherence length is relatively short. If the coherence length is much greater than the layer spacing, reflections from undesirable layers may generate significant cross-talk. Prior art optical storage systems typically utilize a low power CW semiconductor laser diodes as the light source 14. Such light sources have relatively long coherence lengths which are approximately a millimeter. Therefore, the layer spacing required for acceptable levels of cross-talk in the prior art optical storage system of FIG. 1 may be significantly larger than the layer spacing achievable with a short coherence-length source. Utilizing a short coherence-length source thus may allow higher data storage volume density.

The Rayleigh range is a measure of the distance that a collimated beam travels before the beam begins to diverge significantly due to diffraction spreading. Specifically, the Rayleigh range is defined as the distance which the beam travels from the waist before the beam diameter increases by the square root of two, or before the beam area doubles. The Rayleigh range can be expressed as:

$$z = z_R \equiv \frac{\pi \omega_0^2}{\lambda}$$

where $\lambda$ is the wavelength in the medium and where $\omega_0$ is the input spot size at the waist. The Rayleigh range is equivalent to one half the confocal parameter and is thus the distance where the spot size expands from its waist or narrowest point by a factor of the square root of two.

The direct detection (DD) photo-current generated by the intensity of the reflected light impinging upon the detector 20 may be calculated for a substantially single-spatial-mode receiver by the following expression:

$$i_{DD} = R\langle|E(t)|^2\rangle \left\{ d_i + 2d_i \sum_{l \neq 0} K_l A(t_l) \cos\phi_l + \sum_{l=0} K_l^2 + 2 \sum_{l=0} \sum_{m=l+1 \neq 0} K_l K_m A(t_l - t_m) \cos(\phi_l - \phi_m) \right\}$$

The detector 20 receives only a component of the reflected complex field that projects onto the fundamental (e.g. Gaussian) mode of the receiver. The detector 20 generates a photo-current signal proportional to the magnitude squared of the reflected field component.

The reflected field is the sum of the signal and cross-talk complex phasors. The cross-talk complex phasors are the sum of fields from each interfering data layer. For each interfering data layer, the reflected complex cross-talk field is the product of the incident field and the complex amplitude reflection coefficient. The Gaussian spatial component from layer l is found from the projection (normalized overlap integral) of the reflected field and receiver mode over any common aperture plane. Its contribution is represented by a magnitude, $\kappa_l$, and a phase factor, $\phi_l$. $\kappa_l$ may be calculated from the overlap of the receiver mode and the field reflected from the l-th data layer.

The presence of data alters the reflected field by multiplying it by a data-pattern-dependent complex phase function, which makes $\kappa_l$ a random variable in calculating the cross-talk. Note, in general, $\kappa_l$ will decrease because of geometrical defocusing if the interfering layer is widely separated from the data layer. The statistics of $\kappa_l$, may be found by simulating an ensemble of randomly-generated data patterns. The optical phase factor, $\phi_l$, depends on the defocusing factor and the layer location; it may be considered a uniformly distributed random variable, since the precise spatial location of layer l is not controlled or known within ±half-wavelength.

The intensity is calculated by squaring the field. Resulting products of different field components from different layers are formed. The averages of delayed-field products (fields from different layers) appear as coherence functions, with definition $A(x) = \langle E(0)E^a(x)\rangle$, where the brackets denote the normalized statistical average. For partially-coherent fields, such averages decrease for layers that are more separated, with large values of separation x.

The first term in braces, $d_i$, is the data value to be detected ("signal×signal," assumed to be either 0 or 1). The second sum is the product of signal and cross-talk, and the last two sums result from the product of cross-talk and cross-talk. Of these latter, the term $$\sum_{l \neq 0} x_l^2$$

is the incoherent sum of intensities from individual cross-talk layers. It is always present. The last sum represents cross-talk products among different layers, and decreases with reduced coherence length.

Cross-talk can be reduced by defocusing the reflections from the undesirable layers. Defocusing can be accomplished by reducing the Rayleigh range or by increasing the layer separation. If the data storage layers are separated by many Rayleigh ranges, cross-talk between layers will be low and the stored data may be reliably detected. Cross-talk, however, increases significantly as the data layer spacing approaches a Rayleigh range.

Figure 2:
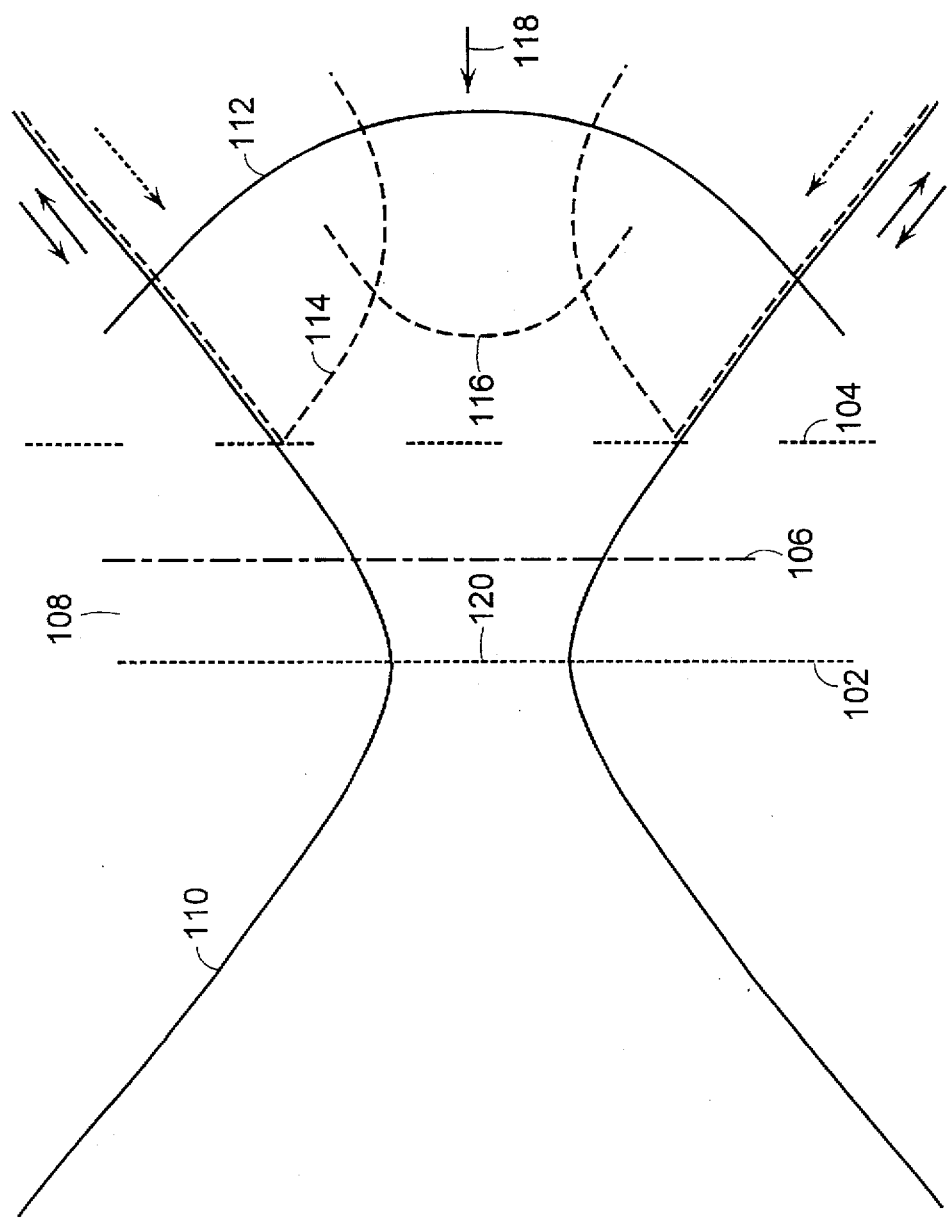
FIG. 2 is a schematic diagram illustrating the mode overlap of a Gaussian light beam reflected from a desired data storage layer, and a Gaussian light beam reflecting from an adjacent interfering data storage layer of an optical storage system embodying this invention.

FIG. 2 is a schematic diagram illustrating a mode overlap 100 of a Gaussian light beam reflected from a desired data storage layer 102 and a Gaussian light beam reflecting from an adjacent interfering data storage layer 104 of an optical storage system embodying this invention. A layer spacing 106 illustrated is approximately twice the Rayleigh range 108 within the storage medium.

A solid curved line 110 represent an equi-intensity contour and a corresponding lighter solid curved line 112 represents an equi-phase contour of the Gaussian light beam reflected from the desired data storage layer 102. A dashed curved line 114 represent an equi-intensity contour and a corresponding lighter dashed curved line 116 represents an equi-phase contour of the Gaussian light beam reflected from adjacent interfering data storage layer 104.

The Gaussian light beam 110, 112 reflected from the desired data storage layer 102 was incident from the right side 118 of the figure and was focused at a desired data layer location 102. The Gaussian light beam 110, 112 was reflected backward from left to right with the same incident and reflected intensity and phase contours. The Gaussian light beam 114, 116 reflected from the adjacent interfering data storage layer 104 was initially identical to the Gaussian light beam 110, 112 but was reflected from the adjacent interfering data storage layer 104.

FIG. 3 illustrates results of theoretical calculations of generalized signal probabilities density function for an optical storage system having cross-talk from two adjacent layers on either side of the desired data storage layer. In this example, the layer thickness was chosen as two times the Rayleigh range within the optical storage medium. The resulting Gaussian mode area for the layers adjacent to the data layer in focus is five times the focus area. The resulting Gaussian mode area for the adjacent layer farthest from the source is seventeen times the focus area.

The calculations were based on a simplified model of the propagation of light within a multilayer optical storage medium. The model includes only the effects of cross-talk. Cross-talk has an average value and a random fluctuating component caused by the interfering data patterns. If the optical field is coherent, the fluctuating component is enhanced because of the complex phasor sum addition of the cross-talk signals. As the optical field becomes less coherent, the fluctuating component approaches a limiting value characteristic of a completely incoherent source, where only the cross-talk intensities add.

Scattering of the read beam as it propagates through the layers has not been included. Detailed numerical propagation simulations have shown this approximation to be valid for relatively low data storage layer reflectivity, which is necessary in multilayer medium having a large number of layers. In addition, the model does not include multi-path reflections. Also, reflective cross-talk has been modeled by including the geometric defocusing factors described in connection with FIG. 2.

The theoretical calculations assumed that the spectrum has a Gaussian spectrum, leading to a Gaussian correlation (fringe visibility) function defined as:

$$R(\Delta x) = exp[-(\Delta x/L_c)^2].$$

Other spectral distributions give rise to other correlation functions, all generally narrow in displacement $\Delta x$ if the spectrum is broad, and characterized by a width $\sim L_c$.

The model includes a stochastic (Monte Carlo) simulation with randomly chosen phase factors for the reflected beam for each data layer, and randomly generated data patterns on the cross-talk layers. This model is useful because coherence effects depend critically on the precise inter-layer phase differences. Also, the presence of data on the adjacent interfering data storage layer 104 was assumed to be random with respect to the desired data storage layer 102.

FIG. 3 illustrates normalized signal probabilities for ratios of layer spacing to coherence lengths from 0.5 to 4.0. The signal probabilities are separated into two groups. A zero group 150 represents the statistics for a "0" or a null data point. A one group 152 represents statistics for a "1" or a reflected signal data point. As the ratio of the layer spacing to the coherence length increases, the separation between the zero group 150 and the one group 152 increases and thus the cross talk and bit error rates decrease. Therefore, cross-talk in a multi-layer optical storage systems with a particular layer spacing can be reduced by decreasing the coherence length of the source with respect to the layer spacing of the storage medium.

Cross-talk can also be reduced by defocusing the reflections from the undesirable layers. Defocusing can be accomplished by increasing the layer separation or reducing the Rayleigh range within the optical medium. As the ratio of the layer spacing to the Rayleigh range in the medium increases, the mode overlap decreases and the reduction in the bit error rates caused by reducing the coherence length diminishes. When the layer spacing is less than or approximately equal to the Rayleigh range and the coherence length is much less than the layer spacing, a shorter coherence length will not further reduce the bit error rates.

The calculations illustrated in FIG. 3 show, that for a layer spacing equal to twice the Rayleigh range in the medium ($L/L_r=2$), reliable bit decisions can be made when the coherence length is chosen to be approximately less than the layer spacing ($L/Lc>1$). The calculations illustrated in FIG. 3 show that an apparatus for reading high density optical storage media with multiple data storage layers may be constructed by only slightly modifying existing multilayer optical storage systems. By utilizing a light source with a coherence length that is approximately the same as or smaller than the layer spacing, an optical storage system may be constructed to read high density optical media with multiple data storage layers with acceptable bit error rates. This invention is particularly advantageous because it allows manufacturers to replace existing low-power CW laser diode with relatively inexpensive short coherence length optical sources such as superluminescent diodes.

Although this invention was described in the context of a Gaussian light beam and a particular optical data storage medium and system, it is noted that other beam shapes and optical data storage systems may be used without departing from the spirit and scope of the invention. In particular, multilayer optical tape may be used for the optical storage medium. Furthermore, although superluminescent diodes, mode locked lasers, multi-longitudinal mode laser diode, and rare earth doped amplified spontaneous emission source are described as appropriate short coherence length sources, it is noted that any other short coherence length source having sufficient brightness may be used without departing from the spirit and scope of the invention.

Equivalents

While the invention has been particularly shown and described with reference to specific preferred embodiments, it should be understood by those skilled in the art that various changes in form and detail may be made therein without departing from the spirit and scope of the invention as defined by the appended claims.

What is claimed is:

1. An apparatus for reading data, comprising:
  a) a source of light having a coherence length $L_c$; and
  b) an optical system focusing said light from said source of light onto a preselected layer of an optical medium comprising at least two layers, each layer of said at least two layers containing data and having a spacing L, wherein said spacing L is greater than a Rayleigh range $L_r$ of the optical medium and the optical system thereby substantially reducing coherence between light reflecting from the preselected layer and light reflecting from each other of said at least two layers.

2. The apparatus of claim 1 wherein the data on each layer is binary data.

3. The apparatus of claim 1 wherein said coherence length Lc is less than substantially 50 microns.

4. The apparatus of claim 1 wherein said coherence length Lc is less than said spacing L.

5. The apparatus of claim 1 wherein said spacing L is less than ten times the Rayleigh range $L_r$.

6. The apparatus of claim 1 wherein said spacing L is less than one hundred times the Rayleigh range $L_r$.

7. The apparatus of claim 1 further comprising a detector for measuring alterations in said light reflected from each layer of said at least two layers which are caused by said data.

8. The apparatus of claim 7 wherein the detector detects a substantially single spatial mode.

9. The apparatus of claim 1 wherein said optical system selectively focuses light from said source of light onto one of said at least two layers containing data.

10. The apparatus of claim 1 wherein the source of light is a superluminescent diode.

11. The apparatus of claim 1 wherein the source of light is a mode locked laser.

12. The apparatus of claim 1 wherein the source of light is a rare earth doped amplified spontaneous emission source.

13. The apparatus of claim 1 wherein the source of light is a continuous wave laser diode.

14. The apparatus of claim 1 wherein the optical system forms a single spatial mode.

15. An apparatus for reading data, comprising:
  a) an optical medium comprising at least two layers, each layer of said at least two layers containing data and having a spacing L;
  b) a source of light having a coherence length $L_c$ less than said spacing L; and
  c) an optical system focusing said light from said source of light onto a preselected layer of interest in said optical medium,
    wherein coherence of light reflecting from the preselected layer and light reflecting from each other of said at least two layers is substantially reduced.

16. The apparatus of claim 15 further comprising a detector for measuring alterations in said light reflected from each layer of said at least two layers which are caused by said data.

17. The apparatus of claim 15 wherein the source of light is a superluminescent diode.

18. The apparatus of claim 15 wherein the source of light is a mode locked laser.

19. The apparatus of claim 15 wherein the source of light is a rare earth doped amplified spontaneous emission source.

20. A method of reading data, comprising:
  a) providing a source of light having a coherence length $L_c$; and
  b) focusing said light from said source of light onto a preselected layer of an optical medium comprising at least two layers, each layer of said at least two layers containing data and having a spacing L,
    wherein said coherence length Lc is less than said spacing L so that coherence of light reflecting from the preselected layer and light reflecting from each other of said at least two layers is substantially reduced.

21. The apparatus of claim 20 wherein said coherence length Lc is less than said spacing L.

22. The apparatus of claim 20 wherein said coherence length Lc is less than substantially 50 microns.

23. The method of claim 20 further comprising a step of detecting alterations in said light reflected from each layer of said at least two layers which are caused by said data.

24. A method for reading data, comprising:
  a) providing an optical medium comprising at least two layers, each layer of said at least two layers containing data and having a spacing L;
  b) providing a source of light having a coherence length $L_c$ less than said spacing L; and
  c) focusing said light from said source of light onto a preselected layer of said optical medium so that coherence of light reflecting from the preselected layer and light reflecting from each other of said at least two layers is substantially reduced.

25. The method of claim 24 further comprising a step of detecting alterations in said light reflected from each layer of said at least two layers which are caused by said data.

26. An apparatus for reading data, comprising:
  a) a source of light having a coherence length $L_c$; and
  b) an optical system focusing said light from said source of light onto a preselected layer of an optical medium comprising at least two layers, each layer of said at least two layers containing data and having a spacing L, wherein said spacing L is greater than a Rayleigh range $L_r$ of the optical medium and the optical system.

* * * * *